(12) United States Patent
Moskovitz (10) Patent No.: US 8,409,824 B2
(45) Date of Patent: Apr. 2, 2013

(54) METHIONINE SULFOXIDE ANTIBODIES

(75) Inventor: Jackob Moskovitz, Lawrence, KS (US)

(73) Assignee: University of Kansas, Lawrence, KS (US)

( * ) Notice: Subject to any disclaimer, the term of this patent is extended or adjusted under 35 U.S.C. 154(b) by 225 days.

(21) Appl. No.: 12/574,279

(22) Filed: Oct. 6, 2009

(65) Prior Publication Data

US 2010/0068205 A1    Mar. 18, 2010

Related U.S. Application Data

(62) Division of application No. 11/366,640, filed on Mar. 2, 2006, now abandoned.

(60) Provisional application No. 60/659,649, filed on Mar. 8, 2005.

(51) Int. Cl.
    *G01N 1/30*    (2006.01)

(52) U.S. Cl. ....... 435/69.1; 436/547; 436/548; 435/69.6

(58) Field of Classification Search ........................ None
    See application file for complete search history.

(56) References Cited

U.S. PATENT DOCUMENTS

| | | | |
|---|---|---|---|
| 4,281,061 A | 7/1981 | Zuk et al. | |
| 2003/0051272 A1 | 3/2003 | Schmidt et al. | |
| 2003/0134339 A1 | 7/2003 | Brown | |
| 2003/0219734 A1* | 11/2003 | Buechler | 435/5 |
| 2005/0160488 A1* | 7/2005 | Jung et al. | 800/278 |

OTHER PUBLICATIONS

Swarup et al., The Plant Journal, 1995, vol. 8 (3) p. 359-368.*
Levine et al., *Methionine Residues May Protect Protiens from Critical Oxidation Damage*, Mechanisms of Aging and Development 107 323-332 (1999).
Stadtman et al., Review—*Methonine oxidation and aging*, Biochimica et Biophysica Acta 1703 135-140(2005).
Le et al., *Analysis of Methionine/Selenomethionine Oxidation and Methionine Sulfoxide Reductase Function Using Methionine-Rich Proteins and Antibodies against Their Oxidized Forms*, Biochemistry 47 6685-6694 (2008).
Oien et al., *Detection of oxidized methionine in selected proteins, cellular extracts and blood serums by novel anti-methionine sulfoxide antibodies*, Arch. Biochem. Biophys. 485 35-40 (2009).
Canello et al., *Oxidation of helix-3 methionines precedes the formation of PK resistant PrPSc*, Plos Pathogens 6 (2010).
Sideri et al., *Methionine Oxidation of Sup35 Protein Induces Formation of the [PSI+] Prion in a Yeast Peroxiredoxin Mutant*, J of Biological Chem 286(45) 38924-38931 (2011).
Day et al., *Inactivation of a peroxiredoxin by hydrogen peroxide is critical for thioredoxinmediated repair of oxidized proteins and cell survival*, Mol. Cell 45 398-408 (2012).
Ringman et al., *Plasma methionine sulfoxide in persons with familial Alzheimer's disease mutations*, Dement. Geriatri. Cogn. Disord. 33 219-225 (2012).
Wehr et al., *Wanted and wanting: Antibody against methionine sulfoxide*, Free Radical Biol and Med 53 1222-1225 (2012).

* cited by examiner

*Primary Examiner* — Yunsoo Kim
(74) *Attorney, Agent, or Firm* — Stinson Morrison Hecker LLP (57) ABSTRACT

Antibodies specific for methionine sulfoxide residues on proteins are provided. The antibodies are prepared using methionine-rich zein proteins, which are oxidized, as antigens.

9 Claims, 3 Drawing Sheets

METHIONINE SULFOXIDE ANTIBODIES

CROSS-REFERENCE TO RELATED APPLICATIONS

This application is a divisional of U.S. Provisional Application Ser. No. 60/659,649, filed on Mar. 8, 2005 and patent application Ser. No. 11/366,640, filed on Mar. 2, 2006, which is hereby incorporated herein by reference.

STATEMENT REGARDING FEDERALLY SPONSORED RESEARCH OR DEVELOPMENT

Not applicable.

BACKGROUND OF THE INVENTION

Reactive oxygen species (ROS) can damage proteins, nucleic acids, and lipids. Methionine oxidation is one of the most common posttranslational modifications to proteins mediated by reactive oxygen species (ROS) that may alter protein structure/function. During conditions of oxidative stress, there is an accumulation of methionine sulfoxide (MetO)-containing proteins (MetO-proteins) (Moskovitz 1997, Moskovitz 1998). Insufficient reversal of MetO-proteins to those having unoxidized methionine by the methionine sulfoxide reductase system (Msr family consisting of MsrA and MsrB) may cause certain proteins to loose their function, aggregate, and be toxic to the cell (Moskovitz 1997; Moskovitz 1998; Gabbita 1999; Stadtman 2003). If not properly repaired, such damage may lead to the development of oxidative-stress related diseases. Alternation of methionine residues between their oxidized and reduced form could serve as a mean to control certain proteins function/activity. In addition, it has been suggested that methionines can function as ROS scavenging agents by their cyclic oxidation/reduction in the cell (Stadtman 2002).

The accumulation of damaged proteins (e.g. MetO-protein and protein-carbonyl) as a result of oxidative stress is well documented, especially in msrA null mutants of various species (Moskovitz 1997, Moskovitz 1998; Mostkoviz 2001). Oxidative damage to proteins is considered to be one of the major causes of aging and age-related diseases, and thus mechanisms have evolved to prevent or reverse these modifications. Pathology analysis performed on postmortem Alzheimer's diseased brains revealed higher levels of MetO-protein (Dong 2003) and carbonyl groups that correlated with diminished Msr activity in comparison to control brains (Gabbita 1999).

Identifying MetO targeted proteins will greatly enhance the knowledge about processes leading to cellular malfunction associated with protein damage, thereby providing information that could be pivotal in developing of novel therapeutics for treating oxidative stress-associated diseases. With regard to the effect of methionine oxidation on protein function, only a few specific proteins have identified as in vivo targets for such modification. The proteins include calmodulin (Gao 1998), Ikappa B (Kanayama 2002, Mohri 2002), and the voltage-dependent K (+) channel (Shaker) (Giorba 1997). The current knowledge about the identity of methionine-oxidized proteins, either in their fully damaged state or their intermediate functional stage in vivo, is still very limited.

One of the major reasons for this lack of extensive data is the fact that there is no direct and efficient screening method for the identification of cellular MetO-proteins. To date, specific proteins from biological extracts could be mainly monitored for their MetO moiety by following their purification, amino acid analysis and/or their analysis by mass spectrometry techniques. Several laboratories have attempted to develop antibodies specific to MetO in proteins. However, all such attempts failed, mainly due to the inability of developing an immunogenic MetO-containing antigen.

The present invention is directed to the production of antibodies specific for MetO-proteins. It is anticipated that the development of a new method for MetO-protein analysis will greatly advance research involving post-transnational modification to proteins. More specifically, identification of MetO-proteins in physiological processes that are affected by ROS production (e.g. aging and neurodegenerative diseases) will shed light on cellular processes that can become toxic due to the accumulation of specific methionine-oxidized proteins.

BRIEF SUMMARY OF THE INVENTION

In one aspect, the present invention is directed to novel antibodies that recognize MetO amino acid residues in proteins.

In another aspect, the present invention is directed to the method of making antibodies specific for MetO proteins.

In another aspect, the present invention is directed to the preparation of antibodies specific for MetO by using an antigen comprised oxidized zein proteins. In one aspect, the oxidized modified recombinant protein of the Zea mays high sulfur Zein gene (18 kDa protein (DZS18)) is used as the antigen. The antigen used to generate the antibodies preferably is comprised of at least 23% methionine.

In still another aspect, the present invention is directed of a method of making the antidivies comprising (a) oxidizing a zein protein to provide a methionine sulfoxide containing zein protein; (b) immunizing an animal with the oxidized zein protein or an immunogenic fragment thereof, under conditions to elicit an antibody response; and (c) isolating antibody producing cells from the animal. Suitable oxidizing agents are well known in the art, and a preferred oxidizing agent is hydrogen peroxide.

In yet another aspect, the antibody producing cells are fused with immortalized cells to form monoclonal antibody-producing hybridoma cells.

In a further aspect, the antibodies of the present invention are specific for the MetO residues in proteins such as glutamine synthestase, oxidized glyceraldehyde 3-phosphate dehydrogenase, oxidized calmodulin, Ikappa B, and voltage-dependent K(+) channel.

In another aspect, the present invention is directed to a method for identifying proteins that exhibit increased MetO level with oxidative stress conditions, slenium deficiency, age, age and/or neurodegenerative-associated diseases, or a combination of the above.

In another aspect, the present invention is directed to a kit comprising the isolated antibody for screening for expression of a polypeptide containing methionine sulfoxide.

In still a further aspect, the present invention includes a diagnostic test for a condition or disease associated with the expression of methionine sulfoxide containing polypeptides in a biological sample. The method includes combining the biological sample with the antibodies of the invention, under conditions suitable for the antibody to bind the polypeptide and form an antibody: polypeptide complex, and detecting the complex, wherein the presence of the complex correlates with the presence of the polypeptide in the biological sample.

It is not intended that the present invention be limited to antibodies specific for MetO-proteins from certain animals. In certain embodiments, the antibody is specific for rabbit MetO-proteins (e.g. glyceraldehydes 3-phosphate dehydrogenase, GAPD). In other embodiments, the antibody is specific for human, rodents, primates, yeast, plant, fungi, or bacterial MetO-proteins. That is, the antibody may be used with biological extracts of all kinds containing MetO-proteins.

It is also not intended that the present invention be limited to antibodies generated in a particular animal. A variety of animals are useful for generating the antibodies of the present invention. In one embodiment, the antibody is generated in an animal selected from a mouse, a rat, a horse, a goat, a chicken, and a rabbit. In some embodiments, the antibodies are collected from the blood of the animal.

Further, it is not intended that the present invention be limited to the nature of the antibodies, as a variety of antibody types are contemplated. In one embodiment, the antibodies are monoclonal. In another embodiment, the antibodies are humanized. In other embodiments, the antibodies are chimeric. In a preferred embodiment, the antibodies are polyclonal.

Additional aspects of the invention, together with the advantages and novel features appurtenant thereto, will be set forth in part in the description that follows, and in part will become apparent to those skilled in the art upon examination of the following, or may be learned from the practice of the invention. The objects and advantages of the invention may be realized and attained by means of the instrumentalities and combinations particularly pointed out in the appended claims.

BRIEF DESCRIPTION OF THE DRAWINGS

FIG. 3 shows the detection of MetO-proteins in yeast strains in vivo by using the anti-MetO-DZS18 antibodies. The yeast strains: OP (MsrA overproducing strain) and MT (null mutant msrA strain) were grown in the presence or absence of 1 mM hydrogen peroxide until their growth rate reached 150 klett units. Following their growth, the cells were harvested, extensively washed with PBS, and disrupted in the presence of PBS and proteases inhibitors cocktail (Roche). Thirty micrograms of protein extracts from each strain were subjected to 2% SDS-protein-gel-electrophoresis followed by western blot analysis using the anti-MetO-DZS18 antibodies. To compete for the antibodies' binding to the targeted proteins, the antibodies were incubated in the presence of 10 mM free MetO in a duplicate experiment. This shows that the antibodies can react with one MetO residue since the reactivity of the antibodies toward the proteins was diminished in comparison to the reactivity of the antibodies without the presence of free MetO.

DETAILED DESCRIPTION OF PREFERRED EMBODIMENT

The term "isolated" means that the material is removed from its original environment (e.g., the natural environment if it is naturally occurring). For example, a naturally occurring antibody present in a living animal is not isolated, but the same antibody, separated from some or all of the coexisting materials in the natural system, is isolated.

As used herein, the term "antibody" refers to intact molecules as well as fragments thereof, such as Fab, F(ab')$_2$, and Fv, which are capable of binding the epitopic determinant. Methods of making these fragments are known in the art. (See for example, Harlow and Lane, Antibodies: A Laboratory Manual, Cold Spring Harbor Laboratory, New York (1988), incorporated herein by reference). The term "antibody" includes monoclonal antibodies, polyclonal antibodies, chimeric, or humanized antibodies. The antibodies of the invention can be of any type (e.g., IgG, IgE, IgM, IgD, IgA, and IgY), class (e.g., IgG1, IgG2, IgG3, IgG4, IgA1, and IgA2), or subclass of immunoglobulin molecule. In preferred embodiments, the immunoglobulin molecules of the invention are IgG.

The term "humanized antibody," as used herein, refers to antibody molecules in which amino acids have been replaced in the non-antigen binding regions in order to more closely resemble a human antibody, while still retaining the original binding ability.

The antibodies of the present invention may be generated by any suitable method known in the art. Polyclonal antibodies to the antigen of interest can be produced by various procedures well known in the art. For example, the oxidized zein proteins containing numerous MetO residues can be administered to various host animals including, but not limited to, rabbits, mice, rats, etc. to induce the production of sera containing polyclonal antibodies specific for the antigen. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*. Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling, et al., in: Monoclonal Antibodies and T-Cell Hybridomas 563-681 (Elsevier, N.Y., 1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art. In a non-limiting example, mice or rabbits can be immunized with the MetO-containing zein proteins of the present invention. Once an immune response is detected, e.g., antibodies specific for the antigen are detected in the mouse serum, the mouse spleen is harvested and splenocytes isolated. The splenocytes are then fused by well-known techniques to any suitable myeloma cells, for example, cells from cell line SP20 available from the ATCC. Hybridomas are selected and cloned by limited dilution. The hybridoma clones are then assayed by methods known in the art for cells that secrete antibodies capable of binding a polypeptide of the invention. Ascites fluid, which generally contains high levels of antibodies, can be generated by immunizing mice with positive hybridoma clones.

Accordingly, the present invention provides methods of generating monoclonal antibodies as well as antibodies produced by the method comprising culturing a hybridoma cell secreting an antibody of the invention wherein, preferably, the hybridoma is generated by fusing splenocytes isolated from a mouse immunized with an antigen of the invention with myeloma cells and then screening the hybridomas resulting from the fusion for hybridoma clones that secrete an antibody able to bind a polypeptide of the invention.

If desired, polyclonal or monoclonal antibodies can be further purified, for example, by binding to and elution from a matrix to which the polypeptide or a peptide to which the antibodies were raised is bound. Those of skill in the art will know of various techniques common in the immunology arts for purification and/or concentration of polyclonal antibodies, as well as monoclonal antibodies (See for example, Coligan, et al., Unit 9, Current Protocols in Immunology, Wiley Interscience, 1994, incorporated by reference).

As used herein, the term "specific for" when used in reference to the interaction of an antibody protein or peptide means that the interaction is dependent upon the presence of a particular structure (i.e., the antigenic determinant or epitope) on the protein; in other words the antibody is recognizing and binding to a specific protein structure rather than to proteins in general (i.e. non-specific or background binding).

Example 1

Generation of Plant-Methionine Rich Protein as Antigen

The endosperm of maize (*Zea mays*) seeds contains several classes of alcohol-soluble storage proteins called zeins, which together make up nearly 50% of the total seed protein content. Some Zeins proteins are rich in sulfur amino acids (Met and Cys). Thus, in the present invention, zeins were used in designing a high rich-MetO protein.

Zeins can be separated into four major classes (as determined by their sequence and apparent molecular mass following SDS/PAGE): α (19 and 22 kDa), β (15 kDa), γ (16 and 27 kDa) and δ (10 kDa) Zeins. In this example, a derivative of the gene encoding an 18 kDa Met-rich Zein that is closely related to the 10 kDa Zein protein was used (Swarup 1995). The Zeins proteins, 10 kDa (DZS10) and the 18 kDa (DZS18), share 80% percent similarity and 66% identity while the DZS18 contains 25% of methionine compared with 23% of DZS10 (Swarup 1995). The high percentage of methionine residues in DZS18 makes it the most methionine-rich protein among cereals and legumes (Swamp 1996). Both δ-Zein genes are coordinately and temporally up regulated during endosperm development. Thus, their corresponding proteins are a good source for free methionine supply needed during the plant's later stages of development.

As discussed more fully below, a recombinant of His-tagged DZS18 was overexpressed in *E. Coli*. bacteria and affinity purified on a nickel column. The methionines of the pure recombinant DZS18 were then oxidized by hydrogen peroxide and then injected into a rabbit to create antibodies specifically reacting against MetO-protein.

More specifically, a PCR reaction was performed. The 5'-forward DNA primer started at 5'end of the DZS18 open reading frame (starting 66 bp downstream of the first ATG cogon). The 3'-reverse complement DNA primer was designed to start at the un-translated area forwarding towards the DZS18 stop codon. The 5'-forward primer contained a unique Bam HI restriction site and the 3'-reverse complement primer contained a unique HindIII restriction site. The template was a plasmid harboring the DZS18 gene and its upstream and downstream flanking regions (Swarup 1995) (kindly provided by Dr. J. Messing, Rutgers University, NJ). Taq polymerase, NTPs, and appropriate reaction buffer were also used (Kit purchased from Roche Inc).

Following the PCR reaction performed according to common used conditions, the resulting PCR product was digested with BamHI and HindIII enzymes and sub-cloned into a pQE30 vector (Qiagen) at the complementary restriction sites. This created an open reading frame for a fusion protein between the 6H is tag and the Zein's N-terminus, starting at the DZS18-DNA sequence corresponding to the 22nd amino acid of the protein. The overexpressed protein was then subjected to a nickel column and purified to homogeneity according to the manufacture procedure (BD Biosciences). The purified recombinant protein was oxidized in the presence of 0.3% hydrogen peroxide diluted in water at 37° C. for 2 hours.

The protein was oxidized with 0.3% hydrogen peroxide for about hours at about 37° C. The oxidized protein (MetO-DZS18) was dialyzed against PBS, pH 7.4, to remove remaining oxidant and subjected to amino acid analysis, as previously described (Reddy 1994). The protein was found to be fully oxidized in its methionine moiety.

The confirmed methionine oxidized DZS18 was injected into a rabbit in multiple injections of 100 μg in 2 weeks intervals to produce anti-MetO-DZS18 antibodies. The rabbit was bled following the second injection in between the injections and the titer and specificity of the antibodies was tested by western blot analysis using MetO-DZS18 as a probe as discussed in Example 2.

Example 2

Antibodies Produced Against Meto-DZs318 Show Specificity Towards Proteins Containing MetO In this example, it was demonstrated that the antibodies from Example 1 showed specificity towards the MetO-DZS18 protein and did not react with the non-oxidized form of the protein (DZS18). In addition, the antibodies reacted with several non-homologus proteins in their oxidized forms: rabid glutamine synthetase (GS) (Sigma) and E. coli glyceraldehyde 3-phosphate dehydrogenase (GAPD) (provided by B. Berlett, NIH). This suggests specific reactivity of the antibodies towards methionine sulfoxide residues. All the methionines in the oxidized proteins were found to be oxidized, as judged by amino acid analysis.

Figure 1:
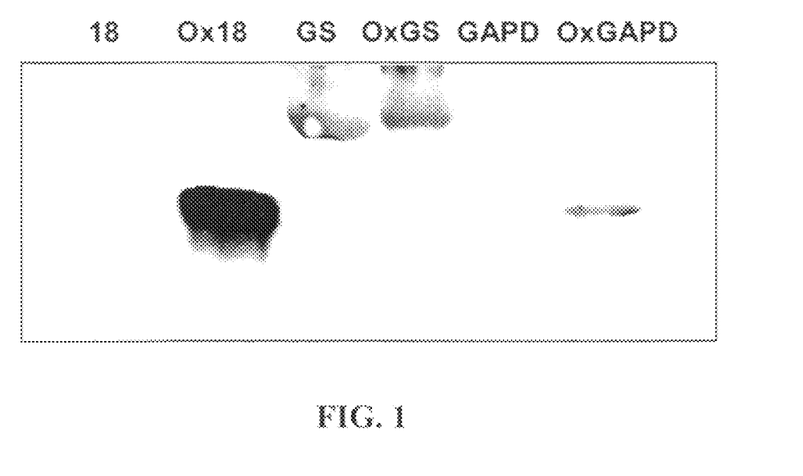
FIG. 1 is a western blot analysis of oxidized and non-oxidized proteins using primary antibodies against MetO-DZS18. Lane 18 shows the non-oxidized DZS18 protein. Lane Ox18 shows the oxidized DZS18. Lane GS shows the native glutamine synthetase (GS) (E. Coli). Lane OxGS shows oxidized GS. Lane GAPD shows native glyceraldehyde 3-phosphate dehydrogenase (Rabbit). Lane OxGAPD shows oxidized GAPD. Five microgram of each protein was subjected to the 4-20% SDS-gel electrophoresis. Oxidation of the proteins was performed using 0.3% of hydrogen peroxide for 2 hours at 37° C. Molecular mass of proteins was as follows: 18: 18 kDa; GS: 50 kDa; GAPD: 36 kDa.

As shown in FIG. 1, the MetO-DNZ18 (Ox18) migrates as a 36-kDa protein due to the mass contribution by the addition of 6-Histidine tag to its N-terminus and oxygen to all of its methionines. The native GS shows reaction with antibodies (FIG. 1) as it is naturally oxidized under its recommended storage conditions at 4° C. However, the oxidized GS (OxGS) reacted slightly stronger with the antibodies and migrated slower in the gel due its enhanced methionine oxidation. Moreover, the reaction intensity of the antibodies with the proteins generally correlates with the percent of the methionine residues in each tested protein (Ox18, 25%; OxGs, 3.6%; and OxGAPD, 3.0%), suggesting full methionine oxidation in all proteins.

The present invention contemplates testing of several other proteins by western blot analysis to evaluate the antibodies binding specificity to pure MetO-proteins. For example, aprotinine (Sigma) (one methionine that is surface exposed), BSA (Sigma), calmodulin (sigma), and Ikappa B will be tested. The latter two proteins contain methionines that their oxidation have shown to alter their function.

Example 3

Specificity of Anti-MetO-DZS18 in Different Tissues

To further characterize the anti-MetO-DZS18 antibodies for detection of MetO-proteins in biological extracts, protein extracts from several mouse tissues were investigated. Each protein extraction was performed in PBS in the presence of proteases inhibitors cocktail (Roche) and 2% SDS. Half of each protein sample was treated with 100 mM hydrogen peroxide for 2 hours at 37° C. in the presence of 2% SDS (to inhibit peroxidases activities). Following 1D-protein-gel-electrophoresis (4-20%) of the proteins, the MetO-proteins were detected in a western blot analysis using the anti-MetO-DZS18 antibodies.

Figure 2:
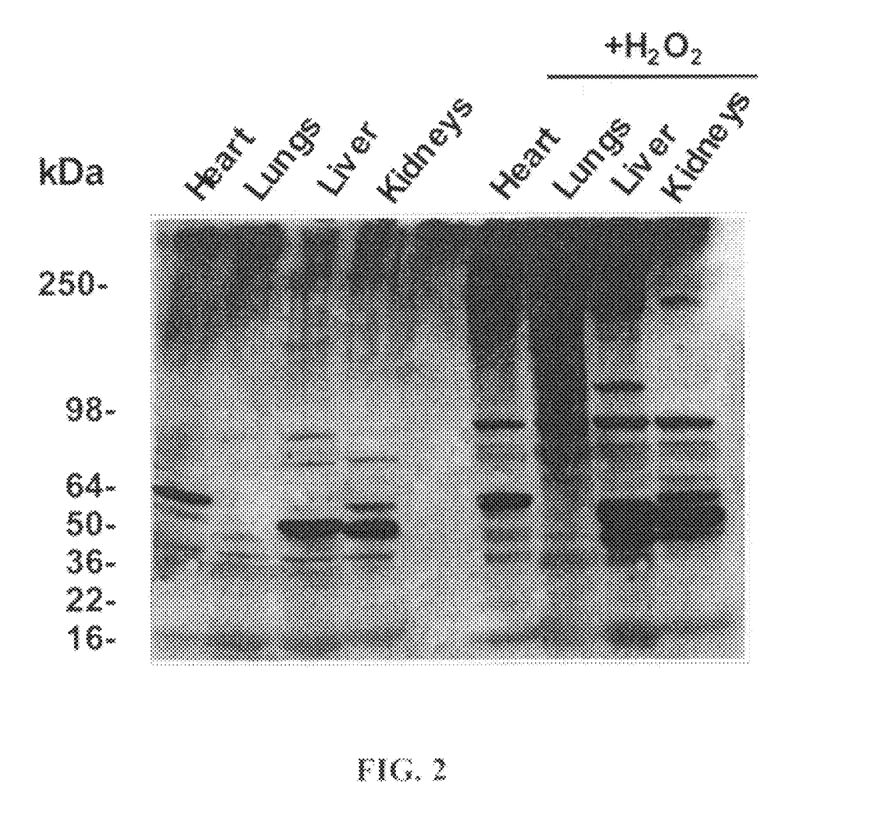
FIG. 2 shows the reaction of anti-MetO-DZS18 with proteins of several mouse tissues with and without exposure to hydrogen peroxide. Protein extracts from several mouse tissues were treated with and without 100 mM hydrogen peroxide. Following SDS-protein-gel-electrophoresis (4-20%) of the proteins, the MetO-proteins were detected in a western blot analysis using the anti-MetO-DZS18 antibodies. kDa indicates masses of the various protein molecular markers.

As expected, as shown in FIG. 2 following western blot analysis using the anti-MetO-DZS18 antibodies, the reaction of the antibodies with existing and new protein bands was increased in all tissues that were treated with hydrogen peroxide in comparison to the non-treated proteins. This result indicates that the anti-MetO-DZS18 antibodies are capable of detecting oxidized proteins in crude extracts due to MetO modification mediated by hydrogen peroxide. The antigen MetO-DZS18 protein does not have any cysteine nor other oxidizable amino acid but methionine and did not show any actual amino acid oxidation but methionine as determined by amino-acid analysis (data not shown). Thus, MetO residues are the only possible binding targets for the antibodies raised against MetO-DZS18.

Example 4

Detection of MetO-Proteins In Vivo Use in Yeast Strains

To determine whether the anti-MetO-DZS18 antibodies are capable of detecting oxidized proteins in vivo, two yeast strains were grown in the presence of absence of 1 mM hydrogen peroxide. One strain was enriched in its MetO-reduction ability (OP, an overproducing strain of MsrA) and a one strain was compromised its MetO-reduction ability (MT, a null mutant strain of msrA: H9strain, Mata ura3-52 his5 leu2). The cells were grown until their growth reached 150 klett units. Following their growth, the cells were harvested, extensively washed with PBS, and disrupted in the presence of PBS and proteases inhibitors cocktail (Roche). Thirty micrograms of protein extracts from each strain were subjected to 1D-protein-gel-electrophoresis followed by western blot analysis using the anti-MetO-DZS18 antibodies. To compete for the antibodies' binding to the targeted proteins, the antibodies were incubated in the presence of 10 mM free MetO in a duplicate experiment.

Figure 3:
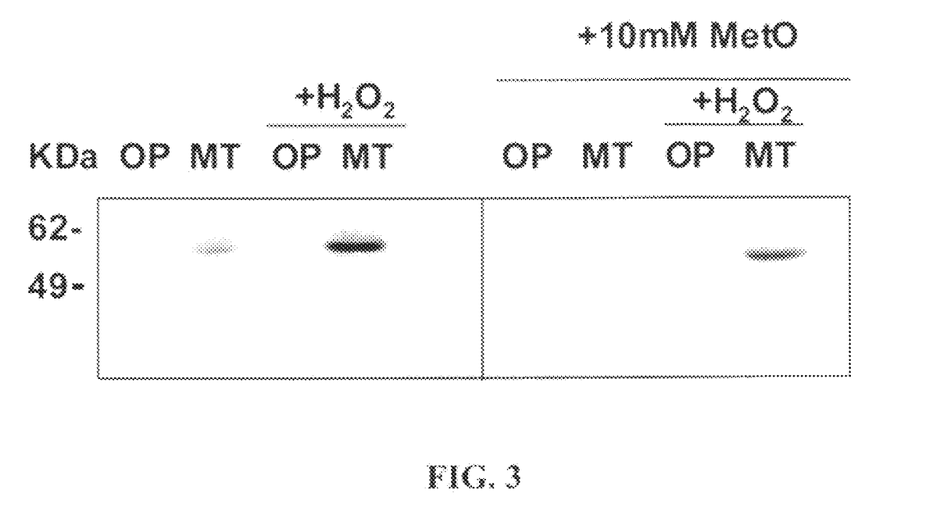

As expected, as shown in FIG. 3, the strain (MT) that was more sensitive to methionine oxidation produced a dominant protein band following reaction with the anti-MetO-DZS18 antibodies even without the hydrogen peroxide treatment. Moreover, the reaction with this protein band that was enhanced following exposure of the cells to hydrogen peroxide. Accordingly, the resistant strain to methionine oxidation (OP) showed no detectable reactions with the anti-MetO-DZS18 antibodies (FIG. 3). The specificity of the antibodies to single MetO residues was confirmed by the fact that when free MetO was co-incubated with the anti-MetO-DZS18 antibodies (during the western blot analysis) the reactivity of the protein band with the antibodies was diminished (FIG. 3); thereby suggesting a competitive binding of the free amino acid with the protein MetO residues on the respected antibodies' binding. The competition was not complete as the competitor is an amino acid rather than protein residue and the antibodies may have subclasses that can bind multiple MetO residues only. Moreover, an identical control experiment performed in the presence of free methionine, instead of free MetO, did not show any change in the reaction of the antibodies with the targeted protein (relative to the reaction without any amino acid, respectively) (data not shown).

The additional presented data provides supportive evidence for the concept that indeed the anti-MetO-DZS18 antibodies are reacting specifically towards multiple and single MetO residues. The average percent of total methionine residues in a protein is only about 2%. Moreover, the percentage of the surface exposed methionine is even lower than 2% as methionine by its nature is a hydrophobic amino acid. Therefore, most of the methionine residues are predicted to be buried within the molecular structure of the protein; thereby less excessive to oxidation by most oxidants.

To enhance the number of the detectable MetO-proteins using the described western blot analysis a combination of two steps will be performed: one is to fractionate and enrich the extracted proteins according to their molecular mass (i.e. to low, medium, and high molecular mass fractions) using an HPLC sizing column techniques; and one is to apply 2D-gel-electrophoresis technique to have a better separation and resolution of the proteins. Combining the two steps is expected to enhance the level of detection of low abundant MetO-proteins.

For example, the proteins can be separated according to their molecular mass by a sizing column (Bio-Rad) using a common HPLC procedure. Eluted proteins will be collected and pooled into three groups of low (5-40 kDa), medium (40-80 kDa), and high (80-200 kDa) molecular mass proteins. Furthermore, each group of proteins will be also separated into additional two groups: one group of proteins that will bind to a Mono-Q column (Pharmacia) in the presence of 50 mM Tris at pH, 7.4 and to one group of proteins that does not bind, respectively. Based on these protein size and charge separations, it is expected that the relative levels of under-representative MetO-proteins will be elevated in all or some of the six groups of proteins relative to their levels in crude extract.

Example 5

Detection of MetO-Proteins In Vivo Use in Human B-Lymphocytes

Figure 4:
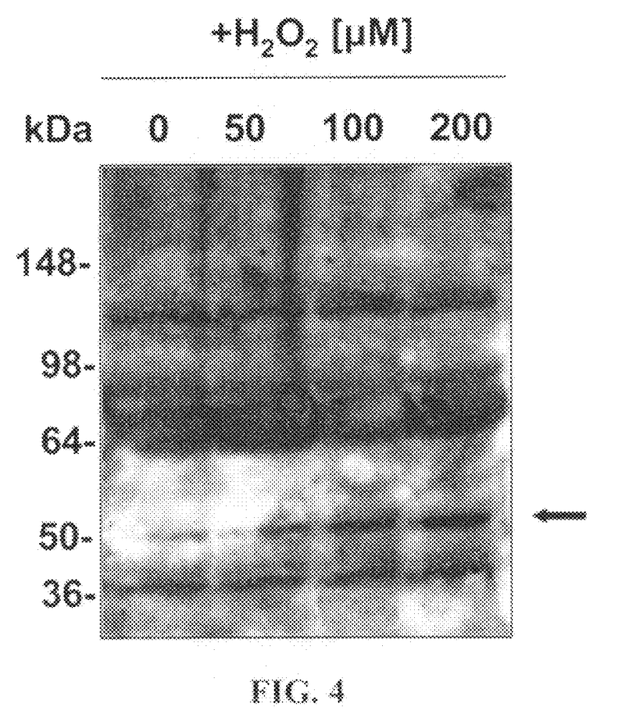
FIG. 4 shows the detection of MetO-proteins in human B-cell lymphocytes in vivo by using the anti-MetO-DZS18 antibodies. Human B-cell lymphocyte cell lines were grown in the absence or presence of elevated concentrations of hydrogen peroxide for about two hours at about 37° C. Following the incubations the cells were extensively washed with PBS and then disrupted in PBS in the presence of proteases inhibitors cocktail (Roche). Thirty micrograms of protein extracts from cells exposed to each treatment were subjected to SDS-protein-gel-electrophoresis followed by western blot analysis, using the anti-MetO-DZS18 antibodies. kDa indicates masses of the various molecular markers. The arrow marks the migration position of the 50 kDa-protein.
Figure 5:
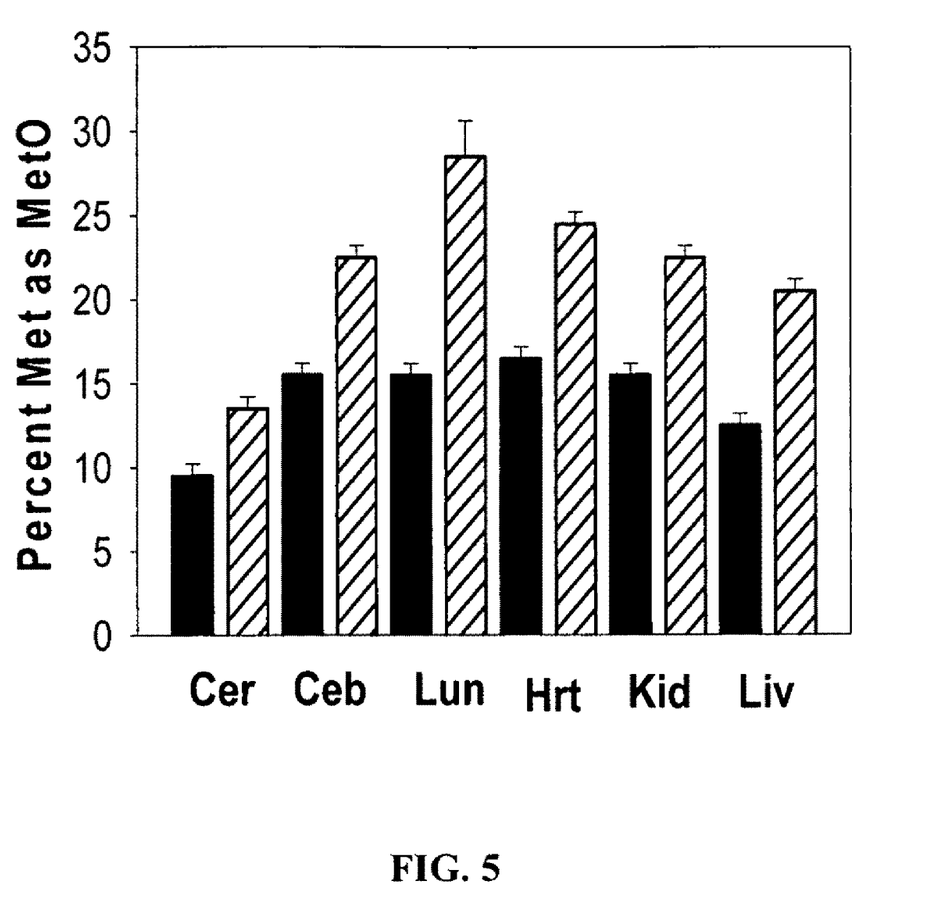
FIG. 5 shows the MetO-protein levels in tissues of wild type and MsrA$^{-/-}$ mouse strains, fed with SD diet. Black or hatched bars represent wild type or MsrA$^{-/-}$ mice, respectively. "Cer" refers to the brain cerebrum; "Ceb" to the brain cerebellum; "Lun" to the lungs; and "Hrt" to the heart. Analysis for MetO-protein was performed using amino acid analysis, according to previously described method (Reddy 1994). Five animals were used for each averaged data point

Similarly, to the use of the yeast strains for in vivo evaluating the anti-MetO-DZS18 antibodies, in this example, human B-lymphocytes cell line was used as a model for MetO-accumulation in human cell culture. The B-lymphocytes cell line was exposed to increasing concentrations of hydrogen peroxide and protein extracts were made following incubation for 2 hours at 37° C. Western blot analysis performed on corresponding protein extracts revealed that even the absence of hydrogen peroxide there were proteins that were recognized to have MetO residues (FIG. 4). However, in parallel to the increased concentrations of the hydrogen peroxide treatment, there was a parallel increase in the staining of a protein band of about 50 kDa as judged by the western blot analysis (FIG. 4). This observation supports the capability of using the anti-MetO-DZS18 antibodies to quantify the MetO levels in specific proteins as a consequence to an elevated level of oxidative stress exposure in vivo.

Prophetic Example 6

Affinity Column

Enrichment and purification of MetO-proteins from biological extracts may be achieved by using a MetO-affinity column that is based on the specific anti-MetO-DZS18 antibodies. The procedure that covalently binds the antibodies to the column and its use for binding and isolating of the targeted proteins will be performed as follows: 0.1 ml of Protein-A coupled matrix (Pierce) will be washed with deionized distilled water (ddW) then with 50 mM sodium borate buffer, pH 8.2. Excess amount of the buffer will be removed. Anti-MetO antibodies (2 mg/ml) will be diluted in 0.1 ml of antibody binding buffer (50 mM sodium borate buffer, pH 8.2) so that the final concentration of antibody will be 0.15 mg/ml. The diluted antibody solution will be added into protein-A conjugated agarose beads and incubated for 30 minutes with gentle mixing. Alternatively, overnight incubation at 4° C. will be employed. Unbound flow through antibody solution will be collected from the column and the gel will be washed five times with 0.1 ml of antibody binding buffer followed by washing with 0.1 ml of cross-linking buffer (0.2M triethanolamine, pH 8.2). An amount of 0.66 mg disuccycinilamide subarate (DSS) will be dissolved in 0.1 ml of cross-linking buffer and will be added to the gel and mixed gently for one hour at room temperature. The gel will be washed five times with 0.1 ml of ddW and drained to a wet cake. A volume of 0.1 ml ethanolamine (0.1M, pH 8.2) will be added into the gel cake and incubated for 10 min at room temperature. The gel will be washed extensively as follows: (1) Five times with 0.1 ml of ddW; (2) Two times with 0.1 ml of 1.0 M NaCl; (3) Two times with 0.1 ml of 0.1 M Glycine, pH 2.8; and (4) Three times with 0.1 ml of ddW.

Finally, the anti-MetO Antibody cross-linked agarose beads will be kept in PBS, p.H7.4, containing 0.02% sodium azide at 4° C. until use. The binding capability of the column to pure proteins will be tested using several proteins, such as rabbit GAPD, E. coli GS, DZS18, aprotinine, BSA, Calmodulin, Ikappa B, and beta-amyloid (AnaSpec, CA) (100 µg each) at their normal or oxidized form. Proteins will be oxidized by 0.3% of hydrogen peroxide for 2 hours at 37° C. and then will be dialyzed against PBS, pH 7.4. Both the oxidized and non-oxidized proteins will be subjected to separated columns, washed with PBS, and eluted with 0.1 M Glycine, pH 2.8. The eluted proteins will be analyzed for their MetO content by amino acid analysis, as previously described (Reddy 1994). It is expected that the oxidized proteins will bind to the columns much more efficiently than their non-oxidized forms, respectively.

The above examples (FIG. 1) showed that GS and GAPD cross-reacted with the antibodies suggesting that even a single MetO residue is being recognized by the antibodies (as both proteins have multiple methionine residues that are located apart from each other). In addition, free MetO was able to compete with the antibodies reactions suggesting that at least some of the antibodies can recognize a single MetO residue (FIG. 3). However, the titer of the specific antibodies raised against single MetO residue may be limited. To overcome this possible limitation and enrich the titer of these antibodies, the antibodies will be affinity purified on a resin that is covalently bound to the N-terminus of the amino acid MetO. The Methionine-resin compound will be purchased from Sigma and swollen in 1 ml of ddW. The MetO-resin will be oxidized with 0.3% of hydrogen peroxide for 2 hours at 37° C., for making the MetO-resin. Following the oxidation, the column will be washed 5 times with 2 ml of PBS. Then, 2 ml of the antibodies will be subjected to the column at slow rate (0.1 ml/min) followed by multiple washing steps (5 washes with 2 ml PBS). Elution of the bound antibodies will be carried out by applying total of 5 ml of 0.1M glycine, pH 2.8 in aliquots of 1 ml. Unbound flow through antibody solution will be collected into vials containing 0.1 ml of 0.1 M Tris, pH 8.0 for pH neutralization purposes. Vials that will show protein absorbance at 280 nm will be selected and dialyzed against PBS, pH 7.4. The resulting antibodies will be then bound to the Protein-A coupled matrix (Pierce) to create the MetO-affinity column, as described above.

Prophetic Example 7

MetO-Protein Pathways

The present invention includes a diagnostic test for a condition or disease associated with the expression of methionine sulfoxide containing polypeptides in a biological sample. The method includes combining the biological sample with the antibodies of the invention, under conditions suitable for the antibody to bind the polypeptide and form an antibody: polypeptide complex, and detecting the complex, wherein the presence of the complex correlates with the presence of the polypeptide in the biological sample.

Biological extracts of yeast and mice tissues will be screened for the existent of MetO-protein. msrA null mutant yeast strain will be grown with and without the presence of 2 mm hydrogen peroxide in the growth media, as previously described (Moskovitz 1997, Moskovitz 2). Cell extracts will be made at early growth rate in PBS buffer, pH 7.4, in the presence of protease inhibitors cocktail (Roche). Equal amounts of proteins from extracts (about 10 mg), made from cell that were and were not exposed to hydrogen peroxide, will be subjected to two separated anti-MetO columns according to the procedure described herein. Proteins eluted from each column will be analyzed for total MetO-protein content by amino acid analysis (Reddy 1994). Alternatively, protein extracts will be divided into three enriched groups of molecular mass proteins: low, medium, and high, using HPLC-sizing and Mono-Q columns, as described in above. Then, the proteins will be separated using 2D-protein-gel-electrophoresis followed by western blot analysis probed with the anti-MetO-DZS18 antibodies. Proteins that will be detected by the antibodies will be extracted from the gel for final identification. In both methods, their identities will be determined by applying LC/MS and common mass spectrometry techniques. Briefly, each purified protein will be subjected to a tryptic digestion. The combination of the molecular masses of the resulting peptides (as determined by mass spectrometry) will provide the digestion pattern information need for the protein identification (using the protein data bank).

It is expected that cells that were treated with hydrogen peroxide will have much higher oxidized proteins than the non-treated cells and may have different MetO-protein profile, respectively. Preliminary results indicate that second-generation of MsrA$^{-/-}$ mice (F2) fed with the SD diet, exhibited substantial higher levels of oxidized proteins than wild type (WT) strain. Accordingly, mouse pups (N=20) from each strain born to breeders (N=4) fed with selenium deficient (SD) diet (yeast extract based diet (22)) will be continuously fed with SD diet. Simultaneously, both mouse strains fed with selenium adequate (SA) diet will be similarly breed to serve as control. All the animals will be raised throughout their life span and differentially euthanized at young (3-6 months), middle (9-12 months) and old age (15-18 months). Protein extracts of lungs, liver, kidney, brain, and heart will be made from each mouse (total of 5 mice for each strain per diet per age). Each tissue will be homogenized in PBS buffer, pH 7.4, in the presence of protease inhibitors cocktail (Roche). The tissue supernatant will be subjected to the anti-MetO columns and the identities of respective eluted-proteins will be determined, as described above for the yeast extracts (using mass spectrometry techniques).

The possibility that the originally designed anti-MetO column will have a lower titer of anti-single-MetO antibodies still exists. As a consequence, possible low protein-binding capabilities of the column may occur. Alternatively, the extracts will be subjected to the enriched anti-single-MetO columns (as described herein) and all the procedures will be followed accordingly. The procedures for enriching proteins by the described biochemical procedures (using the sizing and charge based columns) will result in six groups of protein. It is possible that this protein grouping will not be efficient enough in enhancing the levels of MetO-proteins. In that case, the alternative suggested for above will be applied. Briefly, each crude extract will be separated either by size or charge based column while fractionating the eluted proteins into series of collecting tubes. Each fraction will be subjected to either 1D or 2D-protein-gel-electrophoresis followed by western blot analysis using the anti-MetO-DZS18 antibodies. The identity of each potential MetO-protein will be determined by mass-spectrometry techniques.

The following references are incorporated by reference to the extent that they are needed to teach one skilled in the art how to make and use the invention described herein.

Moskovitz, J., Berlett, S. B., Poston, M., and Stadtman, E. R. "The yeast peptide-methionine sulfoxide reductase functions as an antioxidant in-vivo." *Proc. Natl. Acad. Sci. U.S.A.* 94: 9585-9589, 1997.

Moskovitz, J., Flescher, E., Berlett, S. B., Azare, J. A., Poston, M., and Stadtman, E. R. "Overexpression of peptide-methionine sulfoxide reductase (MsrA) in *Saccaromyces cerevisiae* and human T cells provides them with high resistance to oxidative stress." *Proc. Natl. Acad. Sci. U.S.A.* 95: 14071-14075, 1998.

Gabbita S. P., Aksenov M. Y., Lovell M. A., and Markesbery W. R. "Decrease in peptide methionine sulfoxide reductase in Alzheimer's disease brain". *J. Neurochem.* 73: 1660-1666, 1999.

Stadtman E. R., Moskovitz J., and Levine E. R. "Oxidation of methionine residues of proteins: Biological consequences." *Antioxid. & Red. Signal.* 5: 577-82, 2003.

Swamp S., Timmermans M. C., Chaudhuri S., and Messing J. "Determinants of the high-methionine trait in wild and exotic germplasm may have escaped selection during early cultivation of maize." *Plant J.* 8:359-368, 1995.

Stadtman, E. R., Moskovitz, J., Berlett, B. S., and Levine, R. L. "Cyclic oxidation and reduction of protein methionine residues is an important antioxidant mechanism." *Mol. Cel. Biochem.* 234(1): 3-9, 2002.

Moskovitz, J., Poston, M., Berlett, B. S., Nosworthy, J. N., Szczepanowski, R., and Stadtman. E. R. "Identification and characterization of a putative active site for peptide-methionine sulfoxide reductase (MsrA) and its substrate stereospecificity." *J. Biol. Chem.* 275: 14167-14172, 2000.

Moskovitz, J., Singh, V. K., Requena, J., Wilkinson, B. J., Jayaswal, R. K., and Stadtman, E. R. "Purification and characterization of methionine sulfoxide reductases from mouse and *Staphylococcus aureus* and their substrate stereospecificity." *Biochem. Biophys. Res. Commun.* 290: 62-65, 2002.

Moskovitz, J., Bar-Noy, S., Williams, W., Requena, J., Berlett, B., and Stadtman, E. R. "Methionine sulfoxide reductase (MsrA) is a regulator of antioxidant defense and life span in mammals." *Proc. Natl. Acad Sci. U.S.A.* 98(23): 12920-5, 2001.

Dong J., Atwood C. S., Anderson V. E., Siedlak S. L., Smith M. A., Perry G., and Carey P. R. "Metal binding and oxidation of amyloid-beta within isolated senile plaque cores: Raman microscopic evidence". *Biochemistry* 18; 42: 2768-2773, 2003.

Gao J, Yin D, Yao Y, Williams T. D, and Squier T. C. "Progressive decline in the ability of calmodulin isolated from aged brain to activate the plasma membrane Ca-ATPase". *Biochemistry* 30; 37: 9536-9548, 1998.

Kanayama A., Inoue J., Sugita-Konishi Y., Shimizu M., and Miyamoto Y. "Oxidation of Ikappa Balpha at methionine 45 is one cause of taurine chloramine-induced inhibition of NF-kappa B activation". *J. Biol. Chem.* 5; 277: 24049-24056, 2002.

Mohri, M. S., Reinach, P. S., Kanayama, A., Shimizu, M., Moskovitz, J., Hisatsune, T., and Miyamoto, Y. "Hypochlorite suppresses TNFL-Induced Increase in IL-IL Expression in Human Corneal Epithelial cells." *Investigative Ophthal. & Vis. Sci.* 43: 3190-3195, 2002.

Ciorba, M. A., Heinemann, S. H., Weissbach, H., Brot, N., and Hoshi T. "Modulation of potassium channel function by methionine oxidation and reduction." *Proc. Natl. Acad. Sci. U.S.A.* 2; 94: 9932-9937, 1997.

Haghighi, A. Z., and Maples, K. R. "On the mechanism of the inhibition of glutamine synthetase and creatine phosphokinase by methionine sulfoxide." *J. Neurosci. Res.* 1; 43: 107-111, 1996.

Levine, R. L., Mosoni L., Berlett B. S., and Stadtman E. R. "Methionine residues as endogenous antioxidants in proteins." *Proc. Natl. Acad. Sci. U.S.A.* 24; 93:15036-15040, 1996.

Maier K. L., Matejkova E., Hinze H., Leuschel L., Weber H., and Beek-Speier I. "Different selectivities of oxidants during oxidation of methionine residues in the alpha-1-proteinase inhibitor". *FEBS Lett.* 3; 250: 221-226, 1989.

Butterfield D. A., and Kanski J. "Methionine residue 35 is critical for the oxidative stress and neurotoxic properties of Alzheimer's amyloid beta-peptide 1-42." *Peptides* 23(7): 1299-1309, 2002.

Hokenson, M. J, Uversky, V. N., Goers, J., Yamin, G., Munishkina, L. A., Fink, A. L. "Role of individual methionines in the fibrillation of methionine-oxidized alpha-synuclein." *Biochemistry* 20; 43:4621-4633, 2004.

Newcomb, F. M. Davis, D. A., Moskovitz, J., R., L. Levine, R. L., and Yarchoan, R. "HIV-2 Protease is inactivated following Oxidation at the Dimer Interface and Activity can be Partially Restored with Methionine Sulfoxide Reductase." *Biochem. J.* 346: 305-11, 2000.

Chen, J., and Berry, M. J. "Selenium and selenoproteins in the brain and brain diseases."*J. Neurochem* 86:1-12, 2003.

Moskovitz, J. and Stadtman, E. R. "Selenium deficient diet enhances protein oxidation and affects methionine sulfoxide reductase (MsrB) protein level in certain mice tissues." *Proc. Natl. Acad. Sci. U.S.A.* 100: 7486-7490, 2003.

Reddy, V. Y., Desrochers, P. E., Pizzo, S. V., Gonias, S. L., Sahakian, J. A., Levine, R. L. and Weiss, S. J. "Oxidative dissociation of human alpha 2-macroglobulin tetramers into dysfunctional dimmers". *J. Biol. Chem.* 269: 4683-4691, 1994.

From the foregoing, it will be seen that this invention is one well adapted to attain all ends and objectives herein above set forth, together with the other advantages which are obvious and which are inherent to the invention. Since many possible embodiments may be made of the invention without departing from the scope thereof, it is to be understood that all matters herein set forth are to be interpreted as illustrative, and not in a limiting sense. Thus, while specific embodiments have been shown and discussed, various modifications may of course be made, and the invention is not limited to the specific forms or arrangement of parts and steps described herein, except insofar as such limitations are included in the following claims. Further, it will be understood that certain features and subcombinations are of utility and may be employed without reference to other features and subcombinations. This is contemplated by and is within the scope of the claims.

What is claimed and desired to be secured by Letters Patent is as follows:

1. A method for making antibodies that specifically bind to a methionine sulfoxide residue of a polypeptide, the method comprising:
   a) oxidizing a protein comprising at least 23% methionine residues to provide a methionine sulfoxide containing protein;
   b) immunizing an animal with said methionine sulfoxide containing protein or an immunogenic fragment thereof as an antigen, under conditions to elicit an antibody response; and
   c) isolating antibodies or antibody-producing cells from the animal which specifically bind to a methionine sulfoxide residue of a polypeptide.

2. The method of claim 1 wherein said protein comprised of at least 23% methionine residues is a zein protein.

3. The method of claim 1 further comprising fusing the antibody producing cells with immortalized cells to form monoclonal antibody-producing hybridoma cells.

4. The method of claim 1 wherein said antibodies are polyclonal.

5. The method of claim 1 wherein oxidizing step is performed by exposing the protein to hydrogen peroxide.

6. The method of claim 1 wherein said animal is selected from the group consisting of rabbits, mice, and rats.

7. The method of claim 1 wherein said animal is also administered in an adjuvant.

8. The method of claim 1 wherein said polypeptide is selected from the group consisting of oxidized glutamine synthetase and oxidized glyceraldehyde 3-phosphate dehydrogenase.

9. The method of claim 1 wherein said polypeptide is selected from the group consisting of oxidized calmodulin, Ikappa B, and voltage-dependent K(+) channel.

* * * * *